US007988653B2

(12) United States Patent
Fout et al.

(10) Patent No.: US 7,988,653 B2
(45) Date of Patent: Aug. 2, 2011

(54) ORTHOPEDIC ELBOW BRACE HAVING A LENGTH-ADJUSTABLE SUPPORT ASSEMBLY

(75) Inventors: James M. Fout, Oceanside, CA (US); James D. Burke, Encinitas, CA (US)

(73) Assignee: Breg, Inc., Vista, CA (US)

( * ) Notice: Subject to any disclaimer, the term of this patent is extended or adjusted under 35 U.S.C. 154(b) by 267 days.

(21) Appl. No.: 12/350,403

(22) Filed: Jan. 8, 2009

(65) Prior Publication Data

US 2010/0174220 A1    Jul. 8, 2010

(51) Int. Cl.
*A61F 5/00* (2006.01)
*A44B 19/00* (2006.01)

(52) U.S. Cl. ............ 602/21; 602/20; 602/5; 602/1; 24/593.1

(58) Field of Classification Search .......... 602/1, 5, 602/20, 21, 22, 16, 12, 24, 25, 26, 27, 32; 24/593.1, 593.11, DIG. 43, DIG. 44, DIG. 47; 16/334, 368, 369, 221, 321, 319; 49/188, 49/388, 397
See application file for complete search history.

(56) References Cited

U.S. PATENT DOCUMENTS

| 401,933 | A | 4/1889 | De Camp |
|---|---|---|---|
| 552,143 | A | 12/1895 | Rankin |
| 649,237 | A | 5/1900 | Dyson |
| 1,018,452 | A | 2/1902 | Slaughter |
| 1,780,959 | A | 11/1930 | Wilkes |
| 2,853,999 | A | 9/1958 | Risser |
| 2,958,325 | A | 11/1960 | Claydon et al. |
| 3,698,389 | A | 10/1972 | Guedel |
| 3,805,773 | A | 4/1974 | Sichau |
| 3,913,570 | A | 10/1975 | Madden et al. |
| 4,149,532 | A | 4/1979 | Terry et al. |
| 4,237,873 | A | 12/1980 | Terry et al. |
| D265,248 | S | 6/1982 | Grigorieff |
| 4,370,977 | A | 2/1983 | Mauldin et al. |
| 4,381,768 | A | 5/1983 | Erichsen et al. |
| 4,433,679 | A | 2/1984 | Mauldin et al. |
| 4,481,941 | A | 11/1984 | Rolfes |
| 4,489,718 | A | 12/1984 | Martin |
| 4,531,515 | A | 7/1985 | Rolfes |
| 4,538,595 | A | 9/1985 | Hajianpour |
| 4,559,932 | A | 12/1985 | Salort |
| 4,632,097 | A | 12/1986 | Brooks |
| 4,655,201 | A | 4/1987 | Pirmantgen |
| D291,596 | S | 8/1987 | Detty |
| 4,768,500 | A | 9/1988 | Mason et al. |

(Continued)

FOREIGN PATENT DOCUMENTS

DE    367369    1/1922

(Continued)

*Primary Examiner* — Patricia M Bianco
*Assistant Examiner* — Tarla R Patel
(74) *Attorney, Agent, or Firm* — Rodney F. Brown

(57) ABSTRACT

An adjustable support assembly for an orthopedic brace has a support bar, a housing and a locking mechanism. The housing includes a travel track which receives the support bar. The locking mechanism includes a lock stop and a lock peg array having at least one column and a plurality of rows. The lock stop is perpendicularly positioned between two lock pegs in adjacent rows to prevent displacement of the support bar in the travel track when the length locking mechanism is in the closed position and the lock stop is parallely positioned to enable displacement of the support bar in the travel track when the length locking mechanism is in the open position.

20 Claims, 8 Drawing Sheets

U.S. PATENT DOCUMENTS

| | | |
|---|---|---|
| 4,776,326 A | 10/1988 | Young et al. |
| 4,817,588 A | 4/1989 | Bledsoe |
| 4,982,732 A | 1/1991 | Morris |
| 5,018,514 A | 5/1991 | Grood et al. |
| 5,033,461 A | 7/1991 | Young et al. |
| 5,052,379 A | 10/1991 | Airy et al. |
| 5,138,911 A | 8/1992 | Lan |
| 5,244,455 A | 9/1993 | Swicegood et al. |
| 5,292,303 A | 3/1994 | Bastyr et al. |
| 5,383,844 A | 1/1995 | Munoz et al. |
| 5,385,534 A | 1/1995 | Cassford |
| 5,407,420 A | 4/1995 | Bastyr |
| 5,409,449 A | 4/1995 | Nebelon et al. |
| 5,425,700 A | 6/1995 | Aaserade et al. |
| 5,437,619 A | 8/1995 | Malewicz et al. |
| 5,456,659 A | 10/1995 | Gildersleeve et al. |
| 5,460,599 A | 10/1995 | Davis |
| 5,571,078 A | 11/1996 | Malewicz |
| 5,632,725 A | 5/1997 | Silver et al. |
| 5,645,524 A | 7/1997 | Doyle |
| 5,653,680 A | 8/1997 | Cruz |
| 5,658,241 A | 8/1997 | Deharde et al. |
| 5,658,243 A | 8/1997 | Miller et al. |
| 5,669,873 A | 9/1997 | Towsley |
| 5,672,152 A | 9/1997 | Mason et al. |
| 5,759,165 A | 6/1998 | Malewicz |
| 5,814,000 A | 9/1998 | Kilbey |
| 5,817,040 A | 10/1998 | Hess et al. |
| 5,827,208 A | 10/1998 | Mason et al. |
| 5,848,979 A | 12/1998 | Bonutti et al. |
| D404,818 S | 1/1999 | Cruz |
| 5,885,235 A | 3/1999 | Opable et al. |
| 6,113,562 A | 9/2000 | Bonutti et al. |
| 6,347,817 B1 | 2/2002 | Chou |
| 6,383,156 B1 | 5/2002 | Enzerink et al. |
| 6,533,741 B1 | 3/2003 | Lee et al. |
| 6,599,263 B1 | 7/2003 | Bonutti et al. |
| 6,669,659 B2 | 12/2003 | Dittmer et al. |
| 6,821,261 B2 | 11/2004 | Doty et al. |
| 6,904,915 B2 | 6/2005 | Schuman |
| 6,929,616 B2 | 8/2005 | Bonutti et al. |
| 7,022,094 B2 | 4/2006 | Buckman |
| 7,037,287 B2 | 5/2006 | Cormier |
| 7,097,627 B2 | 8/2006 | Enzerink et al. |
| 7,128,723 B2 * | 10/2006 | Doty et al. ............ 602/16 |
| 7,235,059 B2 | 6/2007 | Mason et al. |
| 2006/0052730 A1 | 3/2006 | Hargrave et al. |
| 2006/0155229 A1 | 7/2006 | Ceriani et al. |
| 2006/0155232 A1 | 7/2006 | Ceriani |
| 2006/0247565 A1 | 11/2006 | Cormier et al. |
| 2007/0100266 A1 | 5/2007 | Hargrave et al. |
| 2007/0225620 A1 | 9/2007 | Carignan et al. |
| 2008/0004556 A1 * | 1/2008 | Gehlbach et al. ............ 602/18 |

FOREIGN PATENT DOCUMENTS

| | | |
|---|---|---|
| FR | 730670 | 1/1934 |
| FR | 2414325 | 1/1978 |
| GB | 19736 | 11/1902 |
| NL | 12997 | 4/1922 |

* cited by examiner

ORTHOPEDIC ELBOW BRACE HAVING A LENGTH-ADJUSTABLE SUPPORT ASSEMBLY

TECHNICAL FIELD

The present invention relates generally to orthopedic braces, and more particularly to an orthopedic elbow brace having a length-adjustable support assembly for the upper arm and/or the lower arm.

BACKGROUND OF THE INVENTION

Orthopedic braces are worn on the body of a user either to support a healthy skeletal joint that is at risk of injury or to stabilize a skeletal joint that has been destabilized by an injury or other condition. Orthopedic braces generally include rigid structural components to support or stabilize the skeletal joint. Frequently, although not necessarily, the rigid structural components are dynamically linked together by one or more hinges enabling controlled pivotal movement of the skeletal joint during user activity or rehabilitative therapy. The orthopedic brace is positioned on the body such that the hinge abuts the skeletal joint, while the rigid components are secured to the body above and below the skeletal joint. Thus, for example, an orthopedic elbow brace is positioned with the hinge of the brace adjacent to the elbow while certain rigid components of the brace are secured to the arm above the elbow and certain rigid components of the brace are secured to the arm below the elbow.

In some instances, it is desirable to enable the user or provider of the orthopedic brace to adjust the dimensions of the rigid components. This feature allows the manufacture of a single adjustable orthopedic brace which is capable of being fitted to a number of different sized users.

Accordingly, it is an object of the present invention to provide an orthopedic brace with rigid supports which have adjustable dimensions. In particular, it is an object of the present invention to provide an orthopedic brace with rigid longitudinal supports for the limbs which have adjustable lengths. It is further an object of the present invention to provide such an adjustable orthopedic brace, wherein adjustment of the rigid supports to alternate adjusted lengths is performed with relative ease. It is another object of the present invention to provide such an adjustable orthopedic brace, wherein the rigid supports reliably maintain their adjusted lengths during normal use of the brace until it is desired to readjust the lengths. These objects and others are accomplished in accordance with the invention described hereafter.

SUMMARY OF THE INVENTION

The present invention is characterized as an orthopedic brace having a length-adjustable support assembly comprising a support bar, a housing and a length locking mechanism. The housing has a travel track which receives the support bar and within which the support bar is linearly displaceable. The length locking mechanism has a lock stop and a lock peg array which includes at least one column and a plurality of rows of lock pegs. The length locking mechanism is selectively transitionable between a closed position and an open position. When the length locking mechanism is in the closed position, the lock stop is essentially perpendicularly positioned relative to the column between two lock pegs in adjacent rows of the lock peg array which prevents linear displacement of the support bar in the travel track. When the length locking mechanism is in the open position, the lock stop is essentially parallely positioned relative to the column which enables linear displacement of the support bar in the travel track.

In accordance with specific embodiments of the present characterization, the lock stop is rotatably mounted on the support bar and the lock peg array is mounted on the housing. More preferably, the lock stop is included in a length lock actuator which is rotatably connected to the support bar while the lock peg array is mounted on and outwardly extends from the housing. The lock peg array preferably has two or more columns and three or more rows of lock pegs. The adjustable support assembly is preferably sized in correspondence with an upper arm or lower arm of a user to enable mounting the adjustable support on the arm below or above an elbow joint of the arm, respectively. The adjustable support assembly preferably further comprises a joint fixed to the support bar or the housing. The joint is preferably a rotational hinge.

Another characterization of the present invention is a method for adjusting the length of a support assembly for an orthopedic brace. The method provides a support assembly having a support bar, a housing and a locking mechanism. The support bar has a longitudinal axis. The housing has a travel track sized to receive the support bar therein. The length locking mechanism has a lock stop and a lock peg array including at least one column and a plurality of rows of lock pegs. The support assembly has a plurality of selected lengths, each selected length corresponding to a different position of the support bar in the travel track.

The support bar is positioned in the travel track at a first position such that the support assembly has a first selected length. The support bar is then displaced in a travel direction in the travel track to a second position while maintaining the lock stop in an essentially parallel position relative to the column of the lock peg array. As such, the support assembly has a second selected length different than the first selected length. The support bar is locked in the second position to maintain the support assembly at the second selected length by repositioning the lock stop to an essentially perpendicular position relative to the column between two lock pegs in adjacent rows of the lock peg array.

In accordance with specific embodiments of the present characterization, the lock peg array is mounted on the housing while the lock stop is rotatably mounted on the support bar. The lock stop is preferably repositioned from the essentially parallel position to the essentially perpendicular position by rotating the lock stop along an axis of rotation. The axis of rotation is preferably essentially perpendicular to the travel direction.

The present invention will be further understood from the drawings and the following detailed description.

DESCRIPTION OF PREFERRED EMBODIMENTS

Figure 1:
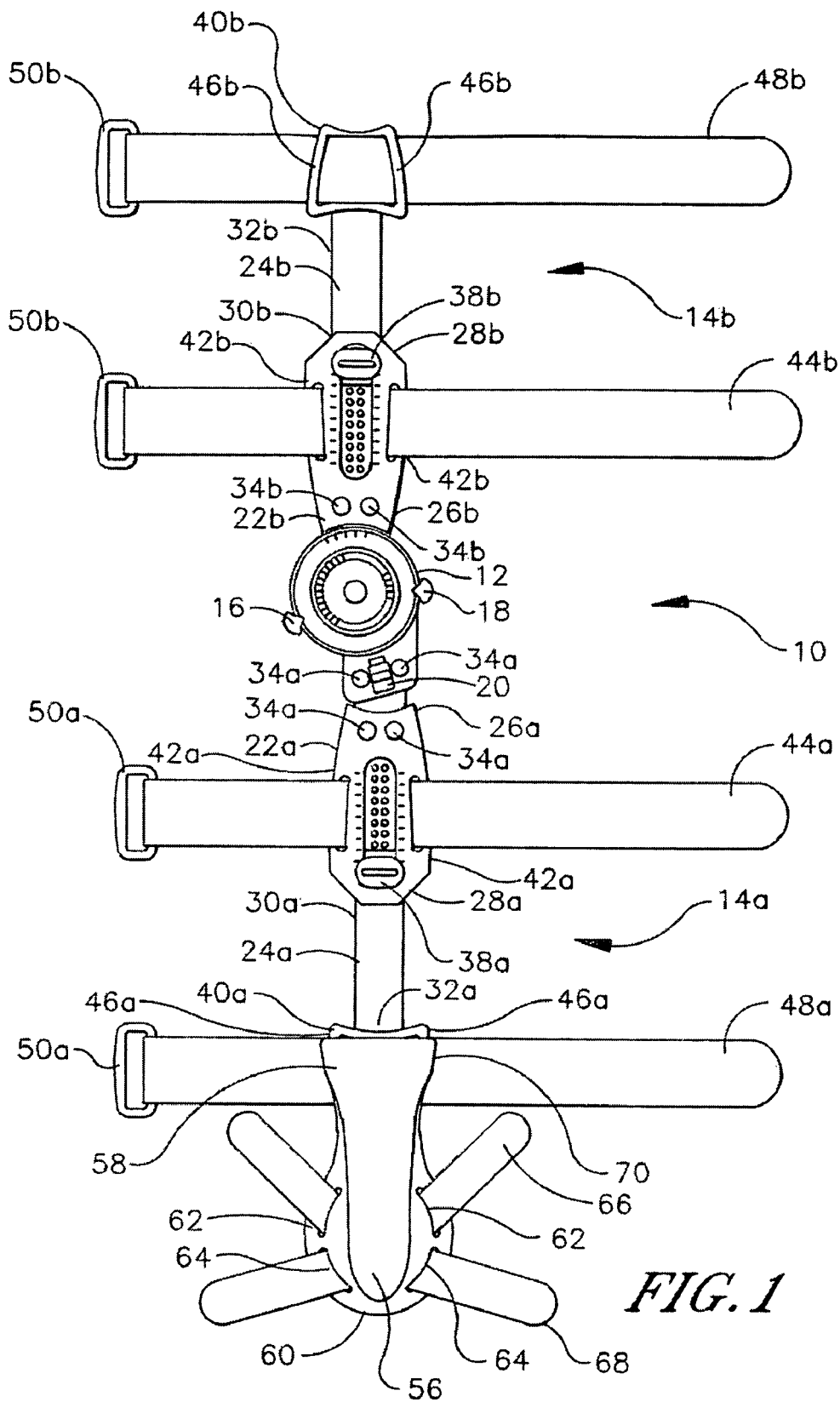
FIG. 1 is a plan view of an orthopedic brace of the present invention.

Referring initially to FIG. 1, an orthopedic brace is shown and generally designated 10. The orthopedic brace 10 comprises a central joint 12, a length-adjustable lower support assembly 14a, and a length-adjustable upper support assembly 14b. The central joint 12 connects the lower support assembly 14a with the upper support assembly 14b such that the lower and upper support assemblies 14a, 14b extend radially from the central joint 12.

There are a number of relative terms defined below which are used in the description of the present invention to distinguish various elements of the orthopedic brace 10 from one another or to distinguish various body parts of a user on which the orthopedic brace 10 is mounted from one another. The definitions are provided solely to add clarity to the description of the invention and are not to be construed as limiting the scope of the invention.

The terms "inside" and "outside" are used herein to describe the relative proximity of a given element or body part to the central longitudinal axis of the body of the user on which the orthopedic brace 10 is mounted. In particular, an "inside" element or body part is closer to the central longitudinal axis of the user's body, while an "outside" element or body part is further from the central longitudinal axis of the user's body. The terms "proximal" and "distal" are used herein to describe the relative proximity of a given element or body part to the central joint 12 of the orthopedic brace 10. In particular, a "proximal" element or body part is closer to the central joint 12, while a "distal" element or body part is further from the central joint 12. The terms "lower" and "upper" are used herein to describe the position of a given element or body part as being either below or above a horizontal plane running through the central joint 12 of the orthopedic brace 10. In particular, a "lower" element or body part is below the horizontal plane running through the central joint 12, while an "upper" element or body part is above the horizontal plane running through the central joint 12.

The central joint 12 is preferably a dynamic joint, which dynamically connects the lower and upper support assemblies 14a, 14b, and is more preferably a rotational hinge, which rotationally connects the lower and upper support assemblies 14a, 14b. The central joint 12 is most preferably a releasably locking rotational hinge with adjustable rotation limits as shown herein. The releasably locking rotational hinge includes a flexion rotation stop 16, an extension rotation stop 18 and a slidable rotational hinge lock actuator 20. Further details of the structure and operation of the releasably locking rotational hinge are disclosed in commonly-owned U.S. Pat. No. 7,235,059 to Mason et al. issued on Jun. 26, 2007, which is incorporated herein by reference.

Notwithstanding the above, it is understood that the central joint 12 is not limited to any one specific construction or type of joint. Thus, most conventional hinges for orthopedic braces, which enable rotation of the lower support assembly 14a and/or the upper support assembly 14b about the hinge, are alternatively employed as the central joint 12 of the orthopedic brace 10. Exemplary prior art hinges are disclosed in U.S. Pat. Nos. 401,933; 4,481,941; 5,672,152; and 5,827,208. In yet another alternative, not shown, the central joint 12 is a static joint which does not enable rotation of the lower support assembly 14a and/or the upper support assembly 14b about the joint. In accordance with this embodiment, the positions of the lower support assembly 14a, upper support assembly 14b, and central joint 12 are all fixed relative to one another and the resulting orthopedic brace 10 functions solely as a splint.

The lower and upper support assemblies 14a, 14b have essentially the same construction. Accordingly, corresponding elements of the lower and upper support assemblies are designated hereafter by the same reference number, but are distinguished from one another by the suffix "a" or "b" which is appended to the reference number. In particular, reference numbers for elements of the lower support assembly 14a have the suffix "a" appended thereto, while reference numbers for corresponding elements of the upper support assembly 14b have the suffix "b" appended thereto.

The lower support assembly 14a includes a lower housing 22a and a lower support bar 24a. The lower housing 22a is an essentially rigid element preferably fabricated from a relatively rigid material, such as a high-strength molded plastic. The lower support bar 24a is likewise an essentially rigid element preferably fabricated from a relatively rigid material, such as a metal and, more particularly, such as aluminum or steel.

The lower housing 22a has a proximal end 26a and a distal end 28a and the lower support bar 24a likewise has a proximal end 30a and a distal end 32a. The proximal end 26a of the lower housing 22a is fixably mounted to the central joint 12 by fixable fasteners 34a, such as rivets (shown herein), screws or the like. As such, the lower housing 22a is essentially fixed against displacement in a linear proximal-distal direction relative to the central joint 12. The distal end 28a of the lower housing 22a has a cross-sectional opening 36a formed therein which is sized and configured in correspondence with the proximal end 30a of the lower support bar 24a to slidably receive the lower support bar 24a into the lower housing 22a. As such, the lower support bar 24a is slidably displaceable in the linear proximal-distal direction relative to the lower housing 22a and central joint 12 in a manner described hereafter.

The lower support assembly 14a additionally includes a lower length lock actuator 38a and a lower strap guide member 40a. The lower length lock actuator 38a is rotatably mounted on a portion of the proximal end 30a of the lower support bar 24a which resides in the lower housing 22a. The lower strap guide member 40a is fixably mounted on the distal end 32a of the lower support bar 24a. The lower length lock actuator 38a and lower strap guide member 40a are both essentially rigid elements preferably fabricated from a relatively rigid material, such as the same high-strength molded plastic from which the lower housing 22a is fabricated. The inside faces of the lower housing 22a and lower strap guide member 40a have an arcuate profile, which corresponds to the contours of the body of a user on which the orthopedic brace 10 is mounted.

A pair of lower housing strap retention loops 42a is integrally formed in the opposite side edges of the lower housing 22a through which a lower housing retention strap 44a is threaded. A pair of lower guide strap retention loops 46a is likewise integrally formed in the opposite side edges of the lower strap guide member 40a through which a lower guide retention strap 48a is threaded. Each lower retention strap 44a, 48a is provided with an integral hook and loop fastener (not shown) commonly termed VELCRO and a strap length-adjusting loop 50a which is sewn onto the end of each respective lower retention strap 44a, 48a. The lower retention straps 44a, 48a, in cooperation with the hook and loop fasteners and strap length-adjusting loops 50a, function to retain the orthopedic brace 10 in close fitting relation with the body of a user in a conventional manner well known to those skilled in the art.

Figure 2:
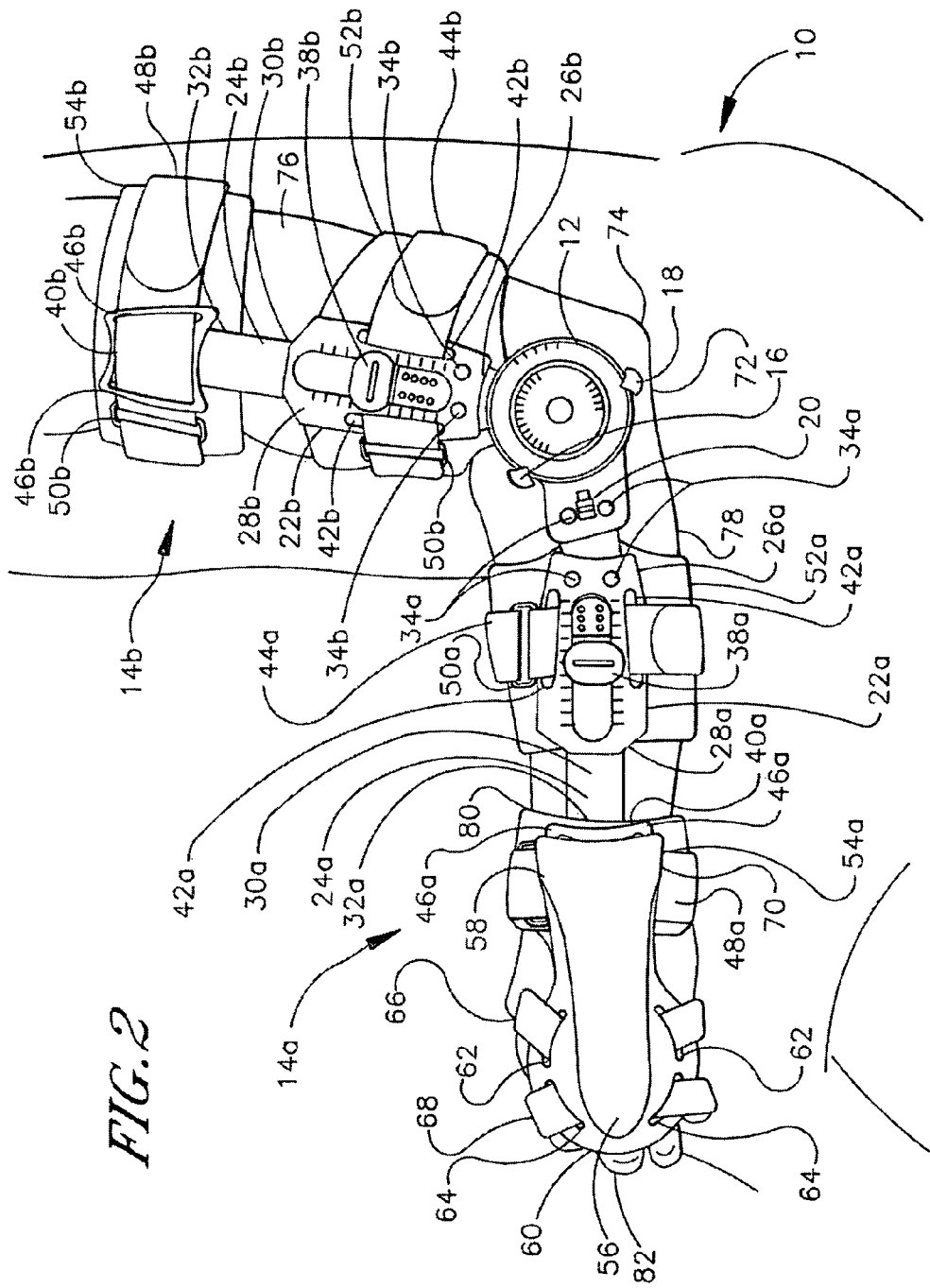
FIG. 2 is a lateral view of the orthopedic brace of FIG. 1 mounted on the arm of a user.

Referring additionally to FIG. 2, a lower housing pad 52a and a lower guide pad 54a (both omitted from FIG. 1 for clarity) are provided in association with the lower housing 22a and lower strap guide member 40a, respectively. The lower pads 52a, 54a are secured to the inside face of the lower housing 22a and lower strap guide member 40a, respectively, by fastening means (not shown), such as hook and loop fasteners (VELCRO). The lower pads 52a, 54a cushion the body of the user from the relatively hard, rigid surfaces of the orthopedic brace 10 when the orthopedic brace 10 is mounted on the body.

The foregoing description of the construction of the lower support assembly 14a applies likewise to the essentially identically constructed upper support assembly 14b. Accordingly, the upper support assembly 14b includes the upper housing 22b and upper support bar 24b. The proximal end 26b of the upper housing 22b is fixably mounted to the central joint 12 by fixable fasteners 34b so that the position of the upper housing 22b is essentially fixed against displacement in the linear proximal-distal direction relative to the central joint 12. The cross-sectional opening 36b formed in the distal end 28b of the upper housing 22b slidably receives the proximal end 30b of the upper support bar 24b into the upper housing 22b so that the upper support bar 24b is slidably displaceable in the linear proximal-distal direction relative to the upper housing 22b and central joint 12.

The upper support assembly 14b additionally includes the upper length lock actuator 38b and upper strap guide member 40b. The upper length lock actuator 38b is rotatably mounted on the portion of the proximal end 30b of the upper support bar 24b which resides in the upper housing 22b. The upper strap guide member 40b is fixably mounted on the distal end 32b of the upper support bar 24b. The upper housing strap retention loops 42b are integrally formed in the opposite side edges of the upper housing 22b through which the upper housing retention strap 44b is threaded. The upper guide strap retention loops 46b are likewise integrally formed in the opposite side edges of the upper strap guide member 40b through which the upper guide retention strap 48b is threaded. Each upper retention strap 44b, 48b is provided with the integral hook and loop fastener and the strap length-adjusting loop 50b. The upper housing pad 52b and upper guide pad 54b (shown in FIG. 2, but omitted from FIG. 1 for clarity) are provided in association with the upper housing 22b and upper strap guide member 40b, respectively.

Figure 3:
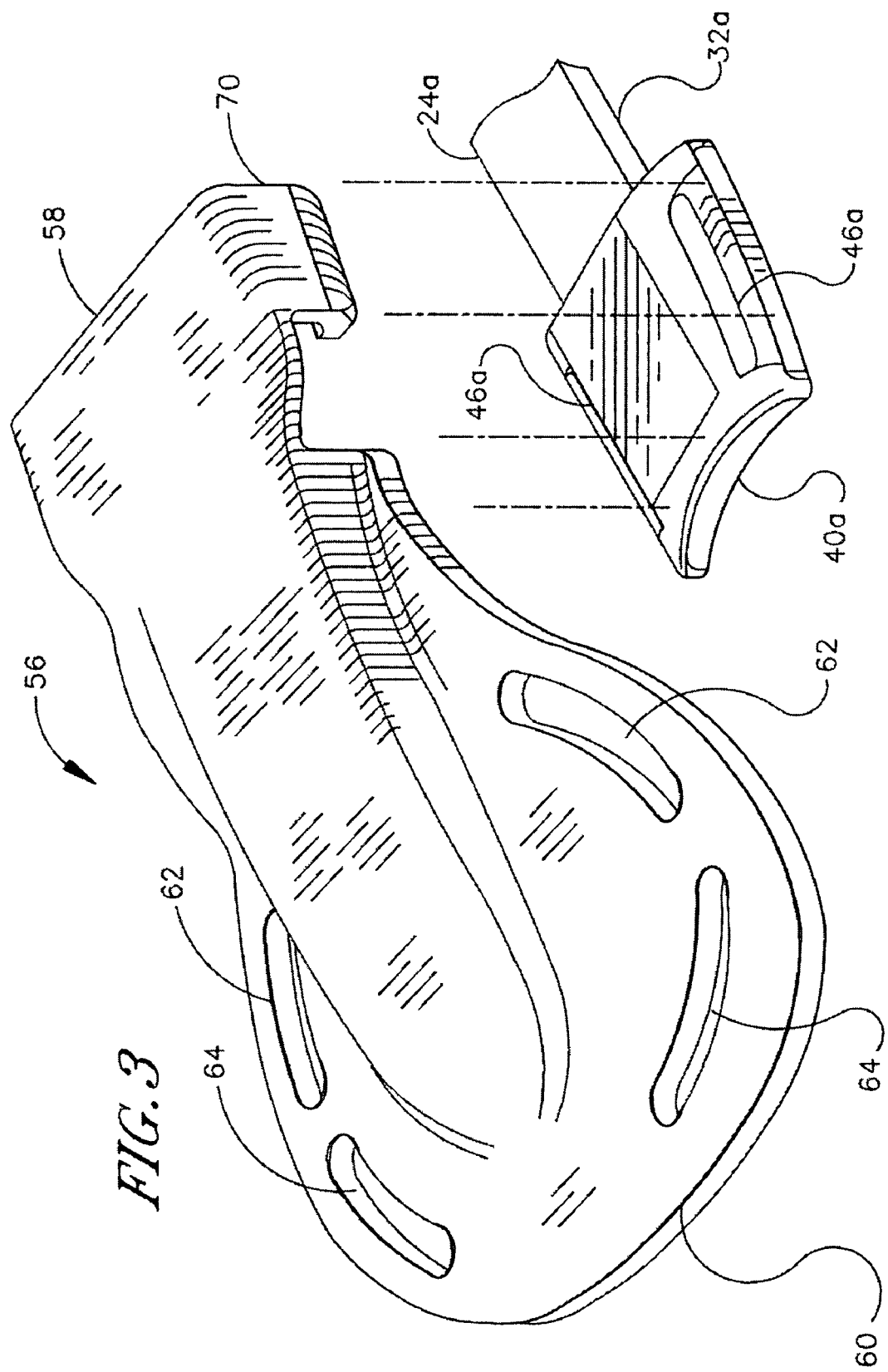
FIG. 3 is a perspective view of the anti-rotation cuff optionally employed in the orthopedic brace of FIG. 1.

The lower support assembly 14a differs from the upper support assembly 14b in that the lower support assembly 14a may additionally include an anti-rotation cuff 56. Referring additionally to FIG. 3, the anti-rotation cuff 56 is an essentially rigid element preferably fabricated from a relatively rigid material, such as the same high-strength molded plastic from which the lower housing 22a, lower length lock actuator 38a and lower strap guide member 40a are fabricated. The anti-rotation cuff 56 has a proximal end 58 and a distal end 60. The proximal end 58 has a narrowed configuration in correspondence with the lower strap guide member 40a and the distal end 60 has a widened configuration in correspondence with the body of a user. A pair of proximal cuff strap retention loops 62 and a pair of distal cuff strap retention loops 64 are integrally formed adjacent one another in the opposite side edges of the distal end 60 of the anti-rotation cuff 56. A proximal cuff retention strap 66 is threaded through the proximal cuff strap retention loops 62 and a distal cuff retention strap 68 is threaded through the distal cuff strap retention loops 64. The cuff retention straps 66, 68 function to retain the anti-rotation cuff 56 in close fitting relation with the body of a user.

The anti-rotation cuff 56 is selectively detachable or attachable to the lower support assembly 14a so that a user can employ the anti-rotation cuff 56 as an integral element of the orthopedic brace 10 or omit the anti-rotation cuff 56 from the orthopedic brace 10 at the option of the user. Selective detachment or attachment of the anti-rotation cuff 56 to the lower support assembly 14a is enabled by a deformable compression clip 70 which is integrally formed on the proximal end 58 of the anti-rotation cuff 56. Attachment of the anti-rotation cuff 56 is effected by press fitting the compression clip 70 onto the side edges of the lower strap guide member 40a at the distal end 32a of the lower support bar 24a. Detachment of the anti-rotation cuff 56 is effected by outwardly deforming the compression clip 70 to release it from its press fit with the side edges of the lower strap guide member 40a.

For purposes of illustration, the orthopedic brace 10 shown and described herein is a specific type of orthopedic brace commonly termed an orthopedic elbow brace. The orthopedic brace 10 is desirably mounted on an arm 72 of a user as shown in FIG. 2. The orthopedic brace 10 is shown by way of example in FIG. 2 as mounted on the left arm 72, which is characterized as having an elbow joint 74, an upper arm 76, and a lower arm (or forearm) 78 including a wrist joint 80 and a hand 82 appended thereto.

When the orthopedic brace 10 is properly mounted on and closely secured to the left arm 72 for the desired function of supporting and/or stabilizing the elbow joint, the central joint 12 is positioned adjacent to the outside (or lateral side) of the elbow joint 74. The specific adjustment of the settings for the flexion rotation stop 16, extension rotation stop 18 and rotational hinge lock actuator 20 is within the purview of the skilled artisan. The upper support assembly 14b is positioned adjacent to the outside (or lateral side) of the upper arm 76 and is longitudinally aligned therewith. The upper retention straps 44b, 48b and the upper pads 52b, 54b snugly encircle the upper arm 76 and the upper retention straps 44b, 48b are tensioned and fastened back onto themselves to desirably maintain the position of the orthopedic brace 10 relative to the arm 72 and substantially inhibit displacement of the upper support assembly 14b relative to the upper arm 76 during normal motion of the arm 72.

The lower support assembly 14a is correspondingly positioned adjacent to the outside (or lateral side) of the lower arm 78 and wrist joint 80 and is longitudinally aligned therewith. The lower retention straps 44a, 48a and the lower pads 52a, 54a snugly encircle the lower arm 78 and the lower retention straps 44a, 48a are tensioned and fastened back onto themselves to desirably maintain the position of the orthopedic brace 10 relative to the arm 72 and substantially inhibit displacement of the lower support assembly 14a relative to the lower arm 78 during normal motion of the arm 72. The anti-rotation cuff 56, if attached to the lower support assembly 14a, is positioned adjacent to the outside (or back) of the hand 82 and is longitudinally aligned therewith. The cuff retention straps 66, 68 snugly encircle the hand 82 and are tensioned and fastened onto themselves to substantially inhibit displacement of the anti-rotation cuff 56 relative to the hand 82 and further to substantially inhibit rotation and flexion of the wrist joint 80 during normal motion of the arm 72.

It is readily apparent to the skilled artisan from the teaching herein that the orthopedic brace 10 is alternatively adaptable for mounting on the right arm (not shown) of the user. It is further apparent to the skilled artisan from the teaching herein that the orthopedic brace 10 is also alternatively adaptable for mounting on either leg (not shown) of the user as an orthopedic knee brace.

Figure 4:
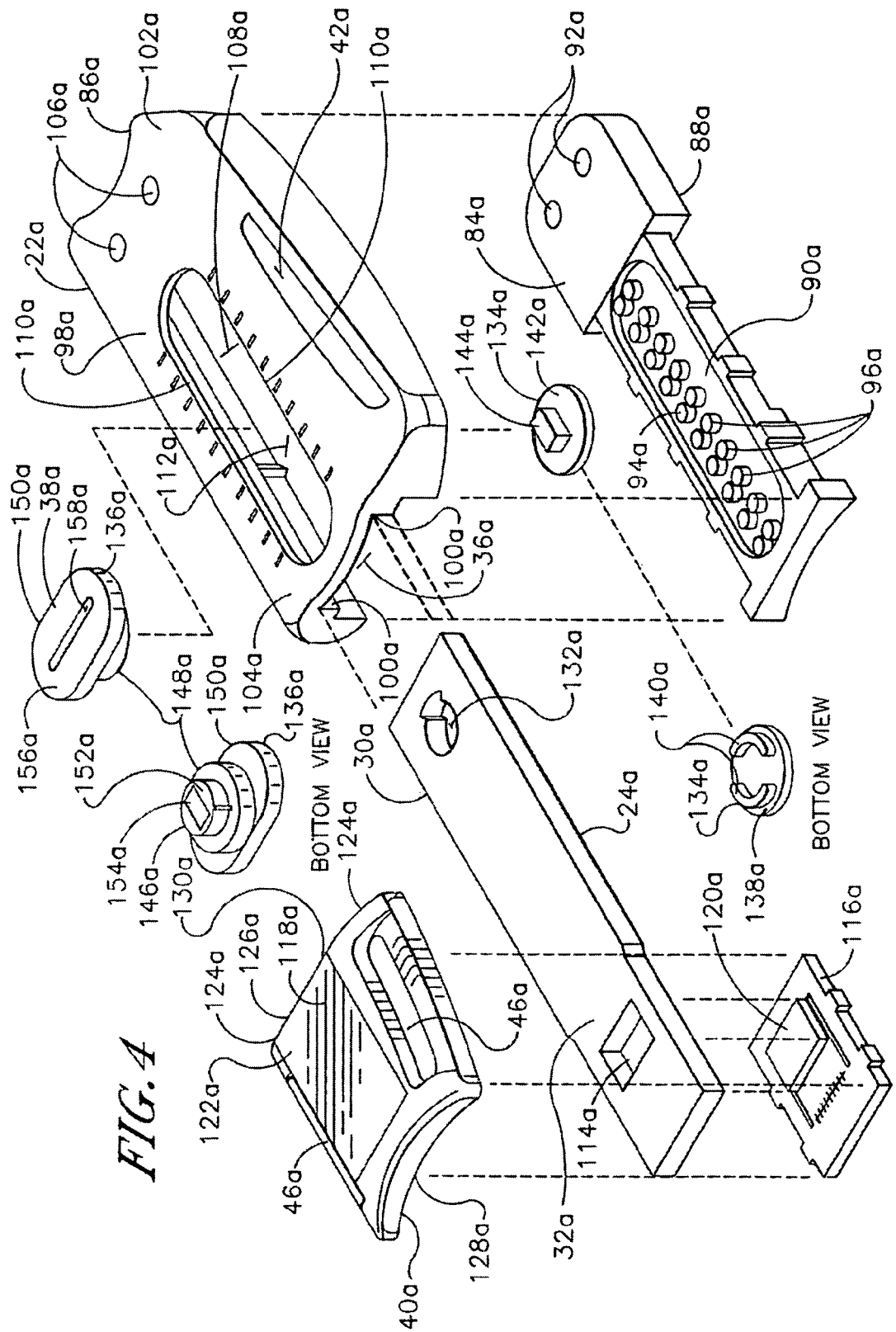
FIG. 4 is an exploded perspective view of the lower support assembly employed in the orthopedic brace of FIG. 1.
Figure 5:
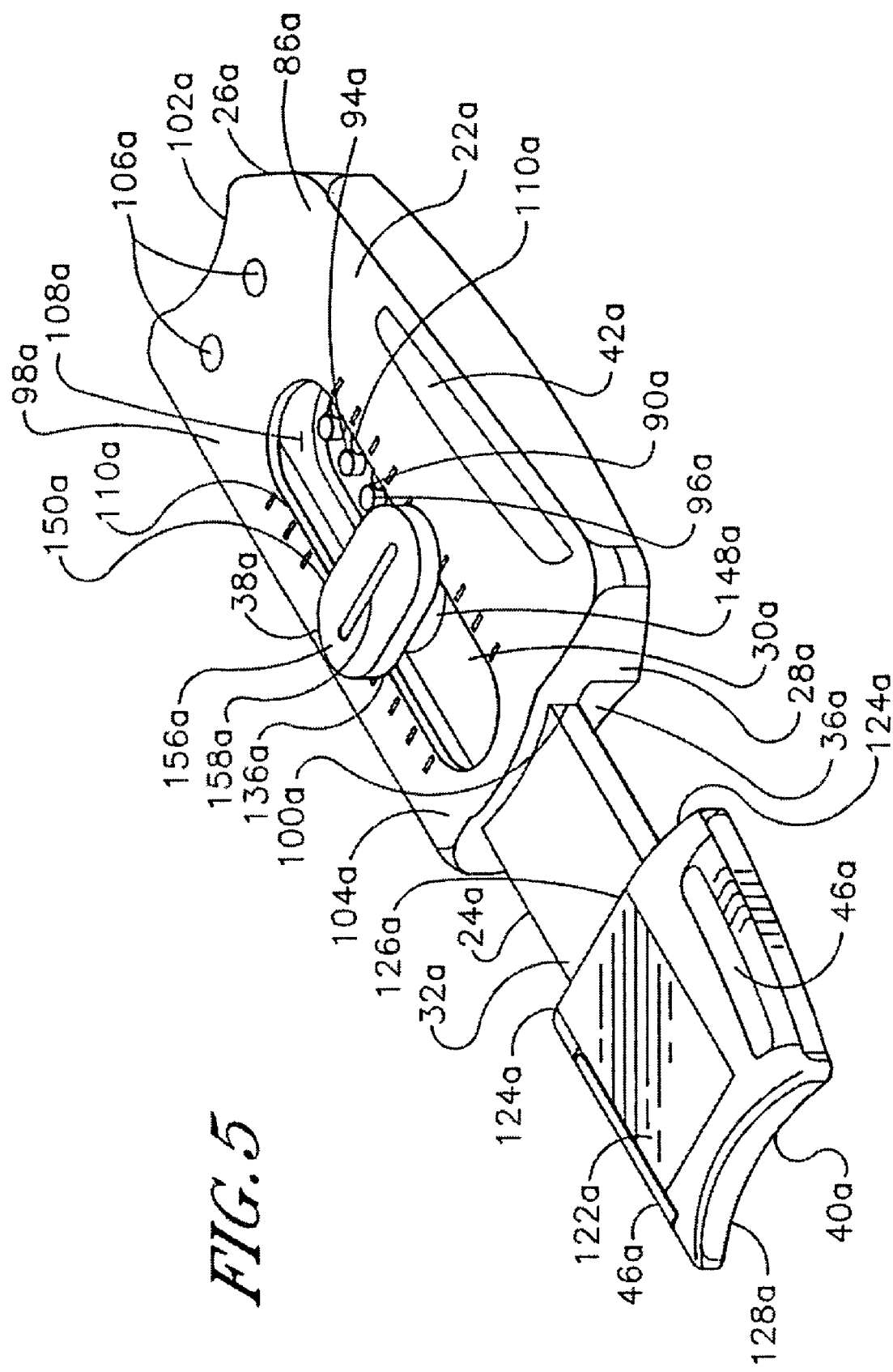
FIG. 5 is an assembled perspective view of the lower support assembly employed in the orthopedic brace of FIG. 1.

Referring to FIGS. 4 and 5, the specific features of the lower support assembly 14a, which enable length adjustment thereof, are shown and described hereafter in greater detail. Since, as noted above, the lower and upper support assemblies 14a, 14b have essentially the same construction, it is understood that the following description of the specific features of the lower support assembly 14a applies likewise to the specific features of the upper support assembly 14b which enable length adjustment thereof.

The lower support assembly 14a comprises the lower housing 22a, lower support bar 24a, lower length lock actuator 38a, and lower strap guide member 40a. The lower housing 22a has a two-piece construction consisting of a housing backing plate 84a and a housing cover 86a, each of which is preferably integrally formed by plastic molding. The housing backing plate 84a has an essentially planar configuration with an outside face 88a, an inside face 90a and a pair of fastening apertures 92a extending therethrough to receive the fasteners 34a. A lock peg array 94a is provided on the outside face 88a of the housing backing plate 84a which consists of a plurality of lock pegs 96a arranged in a pattern of one or more essentially linear horizontal rows and one or more essentially linear vertical columns. Each of the lock pegs 96a in the lock peg array 94a extends outwardly away from the outside face 88a and away from the lower arm 78 when the orthopedic brace 10 is mounted on the arm 72 of a user.

Arrays are commonly characterized by the expression R×C, where R is the number of rows in the array and C is the number of columns in the array. The specific lock peg array 94a shown in FIG. 4 is an 11×2 array. However, it is understood that this specific lock peg array is shown by way of example and not by way of limitation. The present invention is not limited to any specific lock peg array. Instead the present invention contemplates that the skilled artisan designs a lock peg array for the orthopedic brace 10 which has any number of alternative R and C values in accordance with the teaching provided herein. A presently preferred lock peg array is characterized by an R value of 3 or more and a C value of 1 or more. A more preferred lock peg array is characterized by an R value of 3 or more and a C value of 2 or more.

The housing cover 86a has an essentially three-walled configuration including a face plate 98a and a pair of opposing side walls 100a extending orthogonally from the side edges of the face plate 98a. The housing cover 86a also has a proximal end 102a, a distal end 104a, both of which are essentially open, and a pair of fastening apertures 106a extending through the housing cover 86a to receive the fasteners 34a. The face plate 98a has an elongated lock opening 108a extending along the longitudinal axis of the face plate 98a. Opposing edges 110a longitudinally bound the lock opening 108a and define a pair of essentially parallel rails.

The lower housing 22a is assembled into a unitary structure by placing the housing cover 86a over the housing backing plate 84a with the side walls 100a adjacent the side edges of the housing backing plate 84a and press fitting the side walls 100a onto the side edges of the housing backing plate 84a. As such, the proximal and distal ends 102a, 104a of the housing cover 86a correspond to the proximal and distal ends 26a, 28a, respectively, of the lower housing 22a and remain open.

The assembled lower housing 22a maintains a space between the face plate 98a and the outside face 88a of the housing backing plate 84a which delineates a longitudinally extending interior chamber 112a within the lower housing 22a. The interior chamber 112a is partially open to its external surroundings via the lock opening 108a and the open proximal and distal ends 26a, 28a, respectively, of the lower housing 22a. The above-characterized interior chamber 112a acts as a travel track for the lower support bar 24a in a manner described hereafter. When the orthopedic brace 10 is mounted on the arm 72 of a user, the housing backing plate 84a of the lower housing 22a assumes an inside position adjacent to the lower arm 78 while the housing cover 86a assumes an outside position on the opposite side of the orthopedic brace 10 from the lower arm 78.

The lower support bar 24a is a unitary structure, wherein the proximal end 30a is sized and configured to slidably fit through the cross-sectional opening 36a in the distal end 28a of the lower housing 22a. The proximal end 30a of the lower support bar 24a extends into the interior chamber 112a, which enables telescoping slidable linear displacement of the lower support bar 24a relative to the lower housing 22a in the distal-proximal directions along the travel track. The central joint 12 (shown in FIGS. 1 and 2) is similarly sized and configured to fit into the open proximal end 26a of the lower housing 22a. The central joint 12 is provided with fastening apertures (not shown) which align with the fastening apertures 92a, 106a of the housing backing plate 84a and housing cover 86a, respectively, and the fasteners 34a are positioned in the aligned fastening apertures to fixably fasten the central joint 12 to the lower housing 22a.

The lower support bar 24a has a guide member aperture 114a extending through its distal end 32a to fixably receive the lower strap guide member 40a therein. The lower strap guide member 40a has a two-piece construction consisting of a guide backing plate 116a and a guide cover 118a, each of which is preferably integrally formed by plastic molding. The backing plate 116a has an essentially planar configuration, but has a raised rectangular locking tab 120a partially cut away on three sides from the interior of the backing plate 116a. The fourth side of the locking tab 120a remains flexibly attached to the backing plate 116a which enables the locking tab 120a to pivot relative to the backing plate 116a about its attached side.

The guide cover 118a has an essentially three-walled configuration similar to the housing cover 86a. As such, the guide cover 118a includes a face plate 122a and a pair of opposing side walls 124a extending orthogonally from the face plate 122a. The lower guide strap retention loops 46a are integrally formed with the guide cover 118a at a position adjacent to the side walls 124a. The guide cover 118a also has an open proximal end 126a and a closed distal end 128a.

The lower strap guide member 40a is assembled into a unitary structure in substantially the same manner as the lower housing 22a. In particular, the guide cover 118a is placed over the backing plate 116a with the side walls 124a adjacent the side edges of the backing plate 116a and the side walls 124a are press fitted onto the side edges of the backing plate 116a. The assembled lower guide strap member 40a maintains a space between the backing plate 116a and the guide cover 118a which delineates a longitudinally extending interior chamber 130a within the lower guide strap member 40a. The interior chamber 130a is partially open to its external surroundings via the proximal end 126a of the guide cover 118a which remains open after assembly of the lower guide strap member 40a.

The distal end 32a of the lower support bar 24a is sized and configured to fit into the open proximal end 126a of the guide cover 118a. The distal end 32a is slidably displaced through the open proximal end 126a into the interior chamber 130a of the lower guide strap member 40a until the distal end 32a stops up against the closed distal end 128a of the guide cover 118a and the locking tab 120a aligns with the guide member aperture 114a. The locking tab 120a flexibly pivots into the guide member aperture 114a upon alignment which fixably locks the lower guide strap member 40a into attachment with the lower support bar 24a. When the orthopedic brace 10 is mounted on the arm 72 of a user, the backing plate 116a of the lower guide strap member 40a assumes an inside position adjacent to the lower arm 78 while the guide cover 118a assumes an outside position on the opposite side of the orthopedic brace 10 from the lower arm 78.

The lower support bar 24a has a lock actuator aperture 132a extending through its proximal end 30a to rotatably receive the lower length lock actuator 38a therein. The lower length lock actuator 38a has a two-piece construction consisting of an inside actuator member 134a and an outside actuator member 136a, each of which is preferably integrally formed by plastic molding. The inside actuator member 134a is a disc-shaped body, having an outside face 138a with a pair of opposing arcuate lock stops 140a extending inwardly therefrom and having an inside face 142a with a post 144a extending outwardly therefrom.

The outside actuator member 136a has an integral three-tiered construction consisting of an inside tier 146a, an intermediate tier 148a and an outside tier 150a, wherein each tier is progressively wider than the preceding tier when advancing from inside to outside. The inside tier 146a has a disc shape which is sized and configured to rotatably fit into the lock actuator aperture 132a. The inside tier includes an inside face 152a of the outside actuator member 136a which has a receptacle 154a formed therein sized and configured to receive the post 144a of the inside actuator member 134a. The intermediate tier 148a has a disc shape which is substantially similar to that of the inside actuator member 134a. The intermediate tier 148a is sized and configured to slidably and rotatably fit between the longitudinal edges 110a of the lock opening 108a.

The outside tier 150a has an oval shape which is sized and configured to reside above (i.e., outside of) and overlap the longitudinal edges 110a of the lock opening 108a so that it does not substantially engage the longitudinal edges 110a nor impede linearly slidable displacement or rotational displacement of the lower length lock actuator 38a. The outside tier 150a includes an outside face 156a of the outside actuator member 136a. The outside face 156a has a slot 158a formed therein which is sized and configured to receive a tool such as the head of a screw driver or a coin to facilitate manual rotation of the lower length lock actuator 38a.

The lower length lock actuator 38a is assembled into a unitary structure by first positioning the proximal end 30a of the lower support bar 24a in the interior chamber 112a of the lower housing 22a via the cross-sectional opening 36a in the distal end 28a of the lower housing 22a. The post 144a of the inside actuator member 134a and the inside tier 146a of the outside actuator member 136a are inserted into the lock actuator aperture 132a of the lower support bar 24a and the post 144a is press fitted into the receptacle 154a. As a result, the inside tier 146a and enclosed post 144a, which in combination define an inside intermediate tier of the assembled lower length lock actuator 38a, rotatably reside in the lock actuator aperture 132a.

The inside actuator member 134a, which defines an inside tier of the assembled lower length lock actuator 38a, rotatably resides in the interior chamber 112a of the lower housing 22a beneath (i.e., inside of) the lower support bar 24a with the lock stops 140a occupying the same inside position as the lock peg array 94a of the lower housing 22a. The intermediate tier 148a of the outside actuator member 136a, which defines an outside intermediate tier of the assembled lower length lock actuator 38a, rotatably resides in the lock opening 108a. Finally, the outside tier 150a of the outside actuator member 136a, which defines an outside tier of the assembled lower length lock actuator 38a, rotatably resides above (i.e., outside of) the lock opening 108a overlapping the longitudinal edges 110a thereof.

The dynamic lower length lock actuator 38a in combination with the cooperative static lock peg array 94a define a length locking mechanism of the lower support assembly 14a. Operation of the length locking mechanism enables a user to set the lower support assembly 14a in a length adjustment locked state or a length adjustment unlocked state or to transition the lower support assembly 14a between the length adjustment locked and unlocked states. Setting the lower support assembly 14a in the length adjustment locked state corresponds to placing the length locking mechanism in the closed or locked position. Setting the lower support assembly 14a in the length adjustment unlocked state corresponds to placing the length locking mechanism in the open or unlocked position. Transitioning the lower support assembly 14a between the length adjustment locked and unlocked states corresponds to transitioning the length locking mechanism between the closed or locked position and the open or unlocked position.

Figure 6:
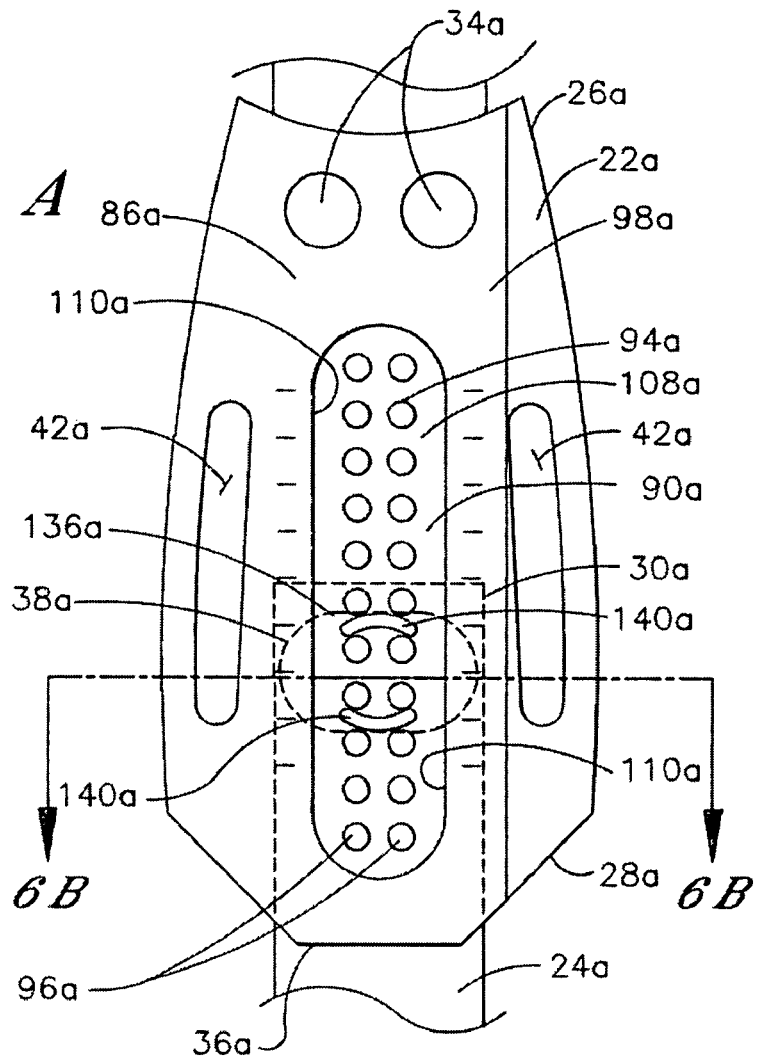
FIG. 6A is a plan view of the lower support assembly employed in the orthopedic brace of FIG. 1, which is in a locked state and at a first adjusted length.
FIG. 6B is a cross-sectional view of the lower support assembly of FIG. 6A taken along line 6B-6B.
Figure 6:
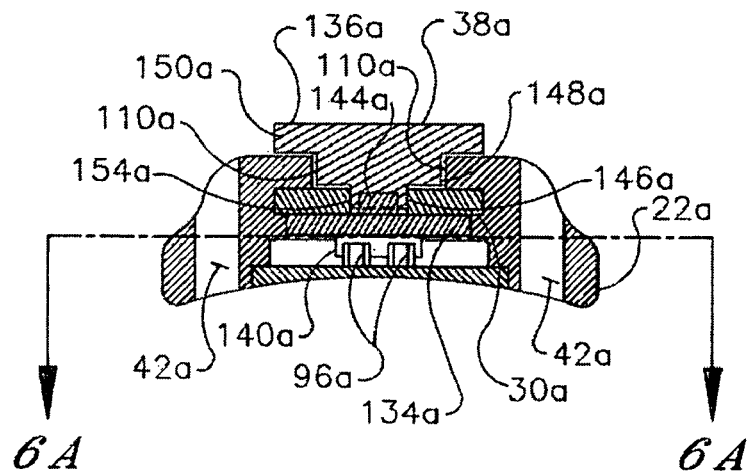

With reference to FIGS. 6A and 6B, setting the lower support assembly 14a in the length adjustment locked state is effected by setting the lower length lock actuator 38a at a first rotation position within the lower housing 22a and lower support bar 24a, wherein each of the lock stops 140a is positioned between two adjacent peg rows in the lock peg array 94a. As such, each lock stop 140a is essentially parallelly aligned with the peg rows and essentially perpendicularly aligned with the peg columns of the lock peg array 94a when the lower length lock actuator 38a is in the first rotation position. Telescoping slidable linear displacement of the lower support bar 24a within the travel track of the lower housing 22a is effectively blocked in either the proximal or distal direction by abutment of each lock stop 140a against the adjacent peg row on the proximal or distal side, respectively, of the lock stop 140a when the lower length lock actuator 38a is in the first rotation position.

Operation of the length lock mechanism by a user of the orthopedic brace 10 enables the user to selectively set the specific adjusted length of the lower support assembly 14a. In particular, the specific adjusted length of the lower support assembly 14a set by the user is determined by the specific adjacent peg rows of the lock peg array 94a the user selects for placement of the lock stops 140a between. In FIGS. 6A and 6B, the user has selectively set the lower support assembly 14a at a desired first adjusted length by selecting the specific pair of adjacent peg rows between which the lock stops 140a are placed that correspond to the first selected length of the lower support assembly 14a.

Figures 7A, 7B:
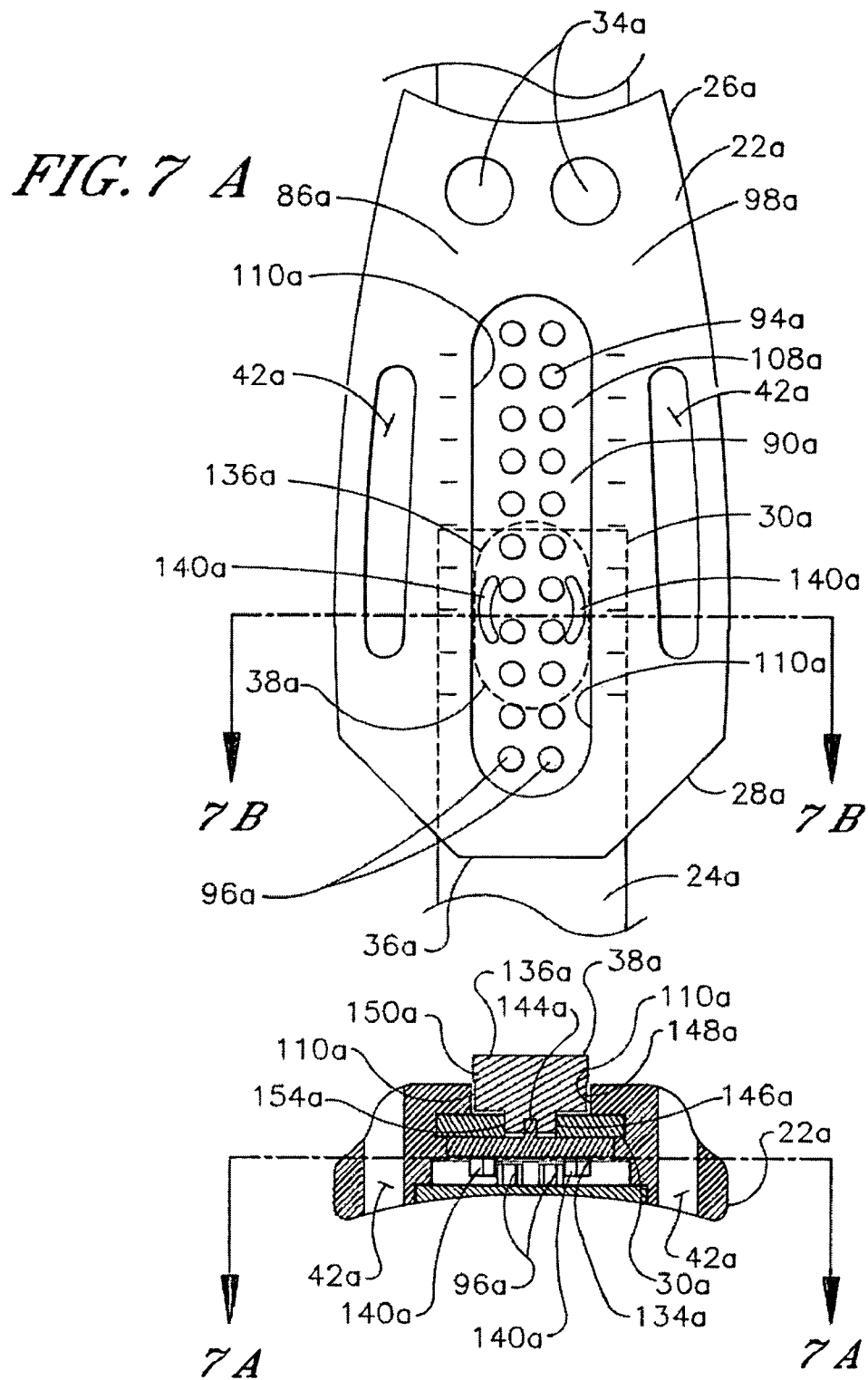
FIG. 7A is a plan view of the lower support assembly employed in the orthopedic brace of FIG. 1, which has been transitioned from the locked state to an unlocked state enabling displacement of the assembly from the first adjusted length to a second adjusted length.
FIG. 7B is a cross-sectional view of the lower support assembly of FIG. 7A taken along line 7B-7B.

Transition of the lower support assembly 14a from the length adjustment locked state to the length adjustment unlocked state is effected by manually rotating the lower length lock actuator 38a within the lower housing 22a and lower support bar 24a (as shown by the rotation displacement directional arrow) from the first rotation position shown in FIGS. 6A and 6B to a new second rotation position shown in FIGS. 7A and 7B so that the lock stops 140a are no longer positioned between two adjacent peg rows in the lock peg array 94a. It is noted that the axis of rotation of the lower length lock actuator 38a is essentially perpendicular to the longitudinal axis of the lower housing 22a and lower support bar 24a.

The second rotation position of the length lock actuator 38a positions each lock stop 140a adjacent to the lock peg array 94a and away from any adjacent peg rows. As such, each lock stop 140a is essentially perpendicularly aligned with the peg rows and essentially parallely aligned with the peg columns (but not necessarily between the peg columns) of the lock peg array 94a when the lower length lock actuator 38a is in the second rotation position. Telescoping slidable linear displacement of the lower support bar 24a within the travel track of the lower housing 22a is effectively enabled in either the proximal or distal direction because the lock stops 140a are unimpeded on either the proximal or distal side when the lower length lock actuator 38a is in the second rotation position.

Figure 8:
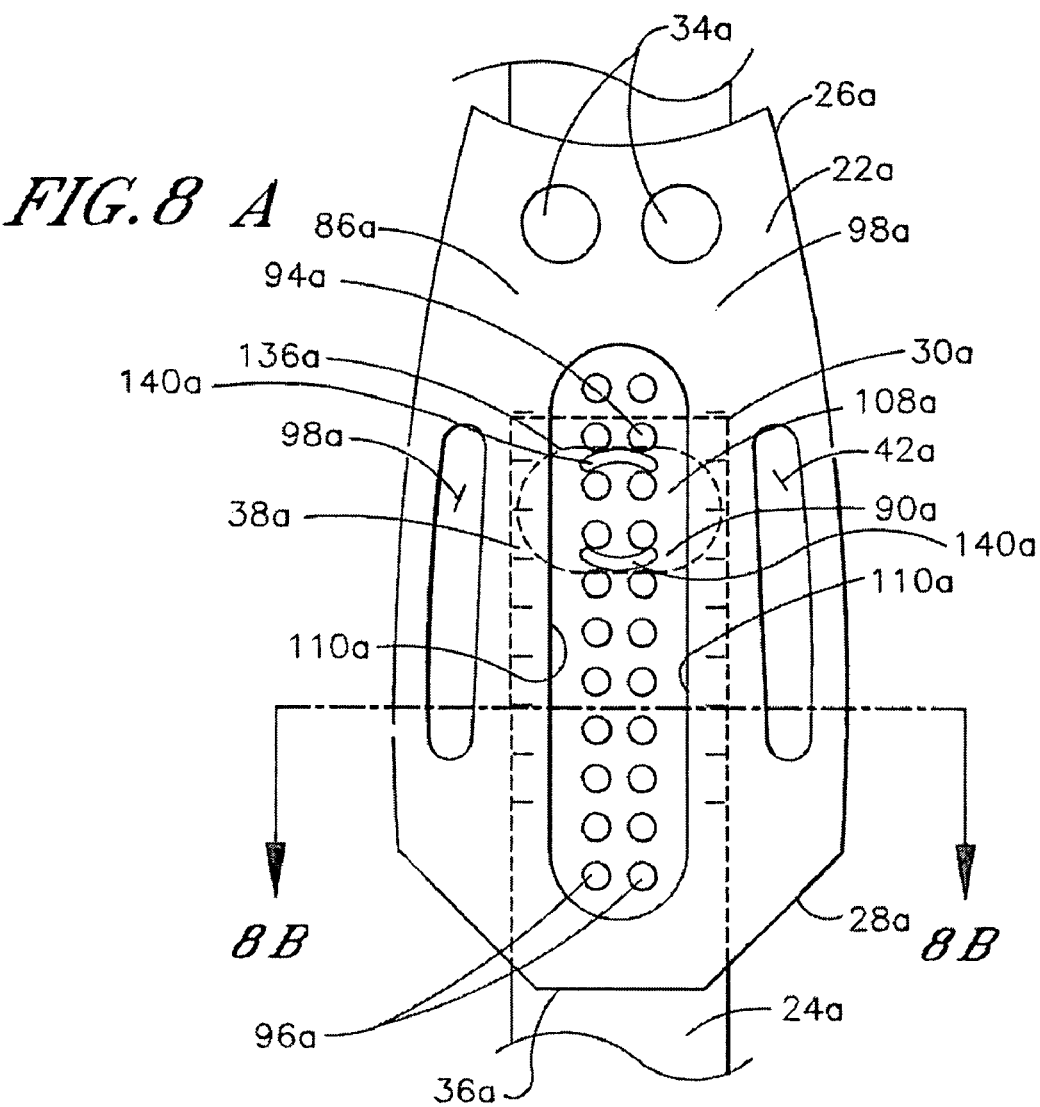
FIG. 8A is a plan view of the lower support assembly employed in the orthopedic brace of FIG. 1, which has been linearly displaced from the first adjusted length to the second adjusted length and which has been transitioned from the unlocked state back to the locked state.
FIG. 8B is a cross-sectional view of the lower support assembly of FIG. 8A taken along line 8B-8B.
Figure 8:
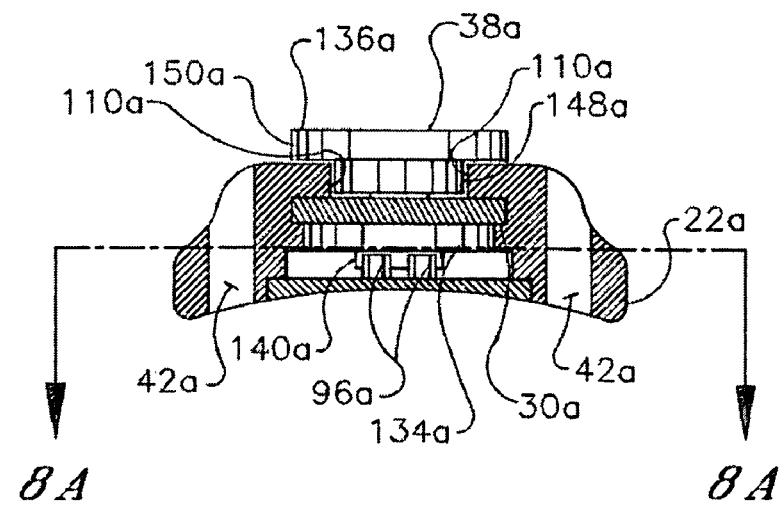

Length adjustment of the lower support assembly 14a from the first adjusted length shown in FIGS. 7A and 7B to a new second adjusted length shown in FIGS. 8A and 8B while the lower support assembly 14a is in the length adjustment unlocked state is effected by manually slidably linearly displacing the lower support bar 24a along the travel track of the lower housing 22a while maintaining the lower length lock actuator 38a in the second rotation position. The direction of linear displacement, termed the travel direction herein, is aligned with the longitudinal axis of the lower housing 22a and lower support bar 24a. Accordingly, the travel direction is essentially perpendicular to the axis of rotation of the lower length lock actuator 38a.

In the case where the second adjusted length is shorter than the first adjusted length as shown in FIGS. 8A and 8B, the lower support bar 24a is pushed (as shown by the linear displacement directional arrow) into the interior chamber 112a of the lower housing 22a via the cross-sectional opening 36a in the distal end 28a of the lower housing 22a until the shorter second adjusted length of the lower support assembly 14a is attained. In the case where the second adjusted length is longer than the first adjusted length (not shown), the lower support bar 24a is pulled from the interior chamber 112a via the cross-sectional opening 36a until the longer second adjusted length of the lower support assembly 14a is attained. The construction of the lower support assembly 14a prevents withdrawal of the lower support bar 24a from the interior chamber 112a of the lower housing 22a in its entirety because the lower length lock actuator 38a acts as a stop against further withdrawal when it abuts up against the distal end 28a of the lower housing 22a.

In any case, once the new adjusted length is attained, the lower length lock actuator 38a is preferably returned to the length adjustment locked state to prevent inadvertent changes to the adjusted length during normal user activity. Transition of the lower support assembly 14a from the length adjustment unlocked state to the length adjustment locked state is effected in essentially the reverse order as described above with respect to transition from the length adjustment locked to unlocked state. The lower length lock actuator 38a is manually rotated within the lower housing 22a and lower support bar 24a from the second rotation position shown in FIGS. 7A and 7B to the first rotation position shown in FIGS. 6A, 6B, 8A and 8B so that the lock stops 140a are returned to their parallel position between two adjacent peg rows in the lock peg array 94a.

It is understood that the foregoing description of operation of the length locking mechanism and the method of length adjustment with respect to the lower support assembly 14a applies likewise to the upper support assembly 14b.

It is further noted that the upper support bar, central joint, and lower support bar in the embodiment of the orthopedic elbow brace described above is a series of discrete interconnected components. However, in accordance with an alternate embodiment of the present invention not shown, either the upper support bar or the lower support bar can be integrally formed with the central joint as a continuous structure, which cooperatively functions with the remaining non-integrated support bar. In accordance with another alternate embodiment of the present invention not shown, the position of any housing and correspondingly paired support bar can be reversed so that the upper housing and/or lower housing is more distal to the central joint than the correspondingly paired upper and/or lower support bar. As such, the support bar is attached to or integral with the central joint rather than the correspondingly paired housing, although the support bar remains slidably displaceable within the housing. In accordance with yet another alternate embodiment of the present invention not shown, the upper housing, central joint, and lower housing (or alternatively upper support bar, central joint, and lower support bar) can be integrally formed together as a single continuous static structure, wherein the resulting orthopedic brace functions as a splint having an adjustable length.

While the forgoing preferred embodiments of the invention have been described and shown, it is understood that alternatives and modifications, such as those suggested and others, may be made thereto and fall within the scope of the invention.

We claim:

1. An adjustable support assembly for an orthopedic brace comprising:
   a support bar;
   a housing including a travel track receiving said support bar; and
   a length locking mechanism including a lock peg array and a lock stop selectively transitionable between a closed position and an open position, said lock peg array having at least one column and a plurality of rows of lock pegs, wherein said lock stop is essentially perpendicularly positioned relative to said column between two lock pegs in adjacent rows of said lock peg array to prevent linear displacement of said support bar in said travel track when said length locking mechanism is in said closed position and said lock stop is essentially parallely positioned relative to said column to enable linear displacement of said support bar in said travel track when said length locking mechanism is in said open position.

2. The adjustable support assembly of claim 1, wherein said lock stop is rotatably mounted on said support bar.

3. The adjustable support assembly of claim 1, wherein said lock peg array is mounted on said housing.

4. The adjustable support assembly of claim 1, wherein said lock peg array has two or more columns.

5. The adjustable support assembly of claim 1, wherein said lock peg array has three or more rows.

6. The adjustable support assembly of claim 1, wherein said lock stop is included in a length lock actuator rotatably connected to said support bar.

7. The adjustable support assembly of claim 1, wherein said lock peg array is mounted on and outwardly extends from said housing.

8. The adjustable support assembly of claim 1, further comprising a joint fixed to said support bar.

9. The adjustable support assembly of claim 8, wherein said joint is a rotational hinge.

10. The adjustable support assembly of claim 1 further comprising a joint fixed to said housing.

11. The adjustable support assembly of claim 10, wherein said joint is a rotational hinge.

12. The adjustable support assembly of claim 1, wherein said adjustable support assembly is sized in correspondence with an upper arm or lower arm of a user to enable mounting said adjustable support on said arm below or above, respectively, an elbow joint of said arm.

13. An adjustable support assembly for an orthopedic brace comprising:
   a support bar;
   a housing including a travel track receiving said support bar; and
   a length locking mechanism including a lock peg array mounted on said housing and a lock stop rotatably mounted on said support bar, said length locking mechanism selectively transitionable between a closed position and an open position, said lock peg array having at least one column and a plurality of rows of lock pegs, wherein said lock stop is essentially perpendicularly positioned relative to said column between two lock pegs in adjacent rows of said lock peg array to prevent linear displacement of said support bar in said travel track when said length locking mechanism is in said closed position and said lock stop is essentially parallely positioned relative to said column to enable linear displacement of said support bar in said travel track when said length locking mechanism is in said open position.

14. The adjustable support assembly of claim 13, wherein said lock peg array has two or more columns.

15. The adjustable support assembly of claim 13, wherein said lock peg array has three or more rows.

16. The adjustable support assembly of claim 13, wherein said lock stop is included in a length lock actuator rotatably connected to said support bar.

17. The adjustable support assembly of claim 13, wherein said lock peg array outwardly extends from said housing.

18. A method for adjusting the length of a support assembly for an orthopedic brace comprising:
   providing a support assembly having a support bar, a housing and a locking mechanism, said support bar having a longitudinal axis, said housing having a travel track sized to receive said support bar therein, said length locking mechanism having a lock stop and a lock peg array including at least one column and a plurality of rows of lock pegs, and said support assembly having a plurality of selected lengths, each selected length corresponding to a different position of said support bar in said travel track;
   positioning said support bar in said travel track at a first position such that said support assembly has a first selected length;
   displacing said support bar in a travel direction in said travel track to a second position such that said support assembly has a second selected length different than said first selected length, while maintaining said lock stop in an essentially parallel position relative to said column of said lock peg array; and
   locking said support bar in said second position to maintain said support assembly at said second selected length by repositioning said lock stop to an essentially perpendicular position relative to said column between two lock pegs in adjacent rows of said lock peg array.

19. The method of claim 18, wherein said lock stop is repositioned from said essentially parallel position to said essentially perpendicular position by rotating said lock stop along an axis of rotation.

20. The method of claim 19, wherein said lock peg array is mounted on said housing, said lock stop is rotatably mounted on said support bar, and said axis of rotation is essentially perpendicular to said travel direction.

* * * * *